(12) United States Patent
Voloshin

(10) Patent No.: US 10,980,267 B2
(45) Date of Patent: Apr. 20, 2021

(54) MOLECULAR PARTICLE SUPERIOR DELIVERY SYSTEM

(71) Applicant: Edward Voloshin, Las Vegas, NV (US)

(72) Inventor: Edward Voloshin, Las Vegas, NV (US)

( * ) Notice: Subject to any disclaimer, the term of this patent is extended or adjusted under 35 U.S.C. 154(b) by 6 days.

(21) Appl. No.: 16/355,681

(22) Filed: Mar. 15, 2019

(65) Prior Publication Data

US 2019/0289895 A1    Sep. 26, 2019

Related U.S. Application Data

(60) Provisional application No. 62/645,388, filed on Mar. 20, 2018.

(51) Int. Cl.
| | | |
|---|---|---|
| *A23L 33/15* | (2016.01) | |
| *A23P 10/30* | (2016.01) | |
| *B82Y 40/00* | (2011.01) | |
| *B82Y 30/00* | (2011.01) | |
| *B82Y 5/00* | (2011.01) | |
| *A61K 47/69* | (2017.01) | |

(52) U.S. Cl.
CPC .............. *A23L 33/15* (2016.08); *A23P 10/30* (2016.08); *A23V 2002/00* (2013.01); *A23V 2200/31* (2013.01); *A23V 2250/705* (2013.01); *A23V 2250/706* (2013.01); *A23V 2250/708* (2013.01); *A23V 2250/7042* (2013.01); *A23V 2250/7052* (2013.01); *A61K 47/6923* (2017.08); *B82Y 5/00* (2013.01); *B82Y 30/00* (2013.01); *B82Y 40/00* (2013.01)

(58) Field of Classification Search
CPC .............................. A23L 33/15; A61K 47/6923
See application file for complete search history.

(56) References Cited

U.S. PATENT DOCUMENTS

| | | | | |
|---|---|---|---|---|
| 2008/0319375 A1* | 12/2008 | Hardy | .................. | A61K 9/1075 604/22 |
| 2011/0236493 A1* | 9/2011 | Canham | .................. | A23P 10/30 424/491 |
| 2017/0112775 A1* | 4/2017 | Dong | .................. | A61K 9/5192 |

* cited by examiner

*Primary Examiner* — Kyle A Purdy
(74) *Attorney, Agent, or Firm* — Bayramoglu Law Offices LLC

(57) ABSTRACT

A nano solid liquid H2O concentrate and method, the concentrate containing molecules of H2O each encapsulating a composite nano particle including selected nutrient particles of nano scale, the composite particles each having a size generally within a range of 12 and 16 nanometers, a bond between the composite particles and respective interior and/or exterior layers of the H2O molecule being stabilized and sealed.

1 Claim, 7 Drawing Sheets
(6 of 7 Drawing Sheet(s) Filed in Color)

US 10,980,267 B2

MOLECULAR PARTICLE SUPERIOR DELIVERY SYSTEM

CROSS REFERENCE TO RELATED APPLICATION

The present applications claims priority to the earlier filed provisional application having Ser. No. 62/645,388, and hereby incorporates subject matter of the provisional application in its entirety.

FIELD OF THE INVENTION

This disclosure relates generally to nano technology and, more particularly, to a nano particle system, concentrate and method of producing same for advanced nutraceutical applications.

BACKGROUND OF THE INVENTION

Conventional nutritional supplements span a broad range of delivery systems, ranging from liquid-based nutritional concoctions and oral vitamins to processing additives for nutritional enrichment of food and beverages, and even skin patches. Regardless of the system for delivery, however, the objective is the same, namely, to provide bioactive molecules that promote health and well-being, and generally make the user feel energized and "good". While traditional supplements and methods have been found useful, the time needed to dissolve some water soluble nutritional compounds, such as vitamin B complex and vitamin C, and the hydrophobic or water-insoluble nature of other nutritional compounds such as vitamin A, vitamin D, vitamin E and various anti-oxidants, has long presented a technological challenge to nutritional delivery in the food and nutraceutical engineering industry.

Concurrently, there is a growing public awareness for healthy nourishment that includes daily amounts, or dosages set according to USDA minimum daily nutritional requirements, of required micronutrients such as vitamins and antioxidants. Since many nutritional compounds are also sensitive to oxidation, and other degradation mechanisms, there is, along with the interest in enriching foods and drinks with health promoting compounds, a trend to exclude potentially harmful compounds, eliminate ingestion of unnecessary vitamins, as well as other substances and additives characteristic of conventional nutritional supplements.

Enrichment of food and beverages with sensitive hydrophobic nutraceuticals have been found challenging for several reasons. First, some nutraceuticals have relatively poor or delayed solubility in water, which necessitates the use of a surface active agent (surfactant). Second, the resulting surfactant-hydrophobic nutraceutical and associated nano vehicle, or nano capsule, must be colloidally stable in the target product environment (e.g., temp, pH, ionic strength) during production and to ensure extended shelf life of the product. Third, hydrophobic nutraceutical-loaded nanoparticles must be as small as possible to minimize the effect on turbidity (visible light scattering). Fourth, if the hydrophobic nutraceutical is sensitive to oxidation, the vehicle should confer protection to retard degradation during product shelf life. Last, materials composing the vehicle and procedures of its formation must be generally recognized as safe for consumption.

With the advent of nano technology, various attempts have been made to improve nutraceutical delivery through nano sized structures. For instance, a polypeptide (e.g., including a dietary supplement) has been formulated by encapsulation in a nano-structure, such as a nanotubule or a nano-capsule.

Other attempts include encapsulation of flavors and active ingredients in hydrophobic nanospheres, in water sensitive microspheres, or in both the nano and microsphere. The encapsulation of different flavors or active agents in the various components of the system, such as nanospheres and microspheres, provides flavor transition (change in flavor character) during the use of the products. Controlled release of the flavors and/or active ingredients comprise solid hydrophobic nanospheres encapsulated in a moisture sensitive microsphere. Such nanospheres are not individually coated by the moisture sensitive microspheres matrix, but are homogenously dispersed in the water sensitive microsphere matrix. Various flavors and active ingredients are be incorporated in the hydrophobic nanosphere matrix, in the water sensitive microsphere matrix, or in both the nano and micro spheres matrices. While providing nano encapsulated compositions in this manner for introduction to any beverage product, e.g., water, soft drinks, juice, milk, tea and coffee, as clear solution, has been found useful, the method has been found complex and difficult to practice and the product therefore expensive to produce.

Further attempts include use of covalently bonded protein-polysaccharides conjugates for nano encapsulation of hydrophobic nutraceuticals. The particles so formed are small enough that, when mixed with a liquid, a clear and transparent solution is obtained. Alternatively, protein (or peptide)-polysaccharide (or oligosaccharide) conjugates are used as nano capsular vehicles for nanoencapsulation of biologically active compounds, particularly nutraceuticals. The protein-polysaccharides conjugates protect both hydrophobic (i.e., water insoluble) and hydrophilic (i.e., water soluble) nutraceuticals, to provide a composition which, when added to a beverage, disperses so as to provide a clear or transparent solution. While beneficial in some contexts, this delivery system has been found to not only have stability issues, but also requires expensive additives and ingredients, with the result of extensive undesirable or unnecessary chemicals being ingested into the user's body.

A stable nutraceutical composition and method are, therefore, desired that not only provide key nutrients and ingredients, but are also makes them readily available, affordable, and manufacturable, and in concentrations that are highly effective for improving the overall health, comfort, vitality, well being, strength and stamina of users. Also desired is a tasteless, colorless and odorless nutraceutical composition that fully and stably disperses in aqueous media for use in food and beverage compositions and the like.

SUMMARY OF THE INVENTION

According to one aspect of this disclosure, there is provided a colorless, odorless, tasteless molecule of $H2O$ encapsulating a composite nano particle, the composite particle including selected nutrient particles of nano scale.

In accordance with another aspect of the disclosure, a colorless, odorless, tasteless molecule of H2O encapsulating a composite nano particle is provided. The composite nano particle consists essentially of selected vitamin particles of nano scale including, but not limited to, sodium ascorbate, methylcobalamine, pyridoxine, thiomine and pantothenic acid.

According to a further aspect of the disclosure, there is provided a colored, fragrant and/or flavored molecule of H2O encapsulating a composite nano particle, the composite particle including selected nutrient particles of nano scale.

In accordance with still another aspect of the disclosure, a colored, fragrant and/or flavored molecule of H2O encapsulating a composite nano particle is provided. The composite nano particle consists essentially of selected vitamin particles of nano scale including, but not limited to, sodium ascorbate, methylcobalamine, pyridoxine, thiomine and pantothenic acid.

According to yet another aspect of the disclosure, a nano solid liquid H2O concentrate containing molecules of H2O is provided, each encapsulating a composite nano particle including selected nutrient particles of nano scale. The composite particles each have a size generally within a range of 12 and 16 nanometers, a bond between the composite particles and respective interior and/or exterior layers of the H2O molecule being stabilized and sealed, the seal having a stability of approximately 100%.

In accordance with still a further aspect of the disclosure, there is provided a nano solid liquid H2O beverage containing molecules of H2O encapsulating a composite nano particle including selected nutrient particles of nano scale. The composite particles each have a size generally within a range of 12 and 16 nanometers, a bond between the composite particles and respective interior and/or exterior layers of the H2O molecule being stabilized and sealed, the seal having a stability of approximately 100%.

According to yet a further aspect of the disclosure, there is provided a colorless, odorless, tasteless concentrate containing molecules of H2O each encapsulating a composite nano particle including selected nutrients, the concentrate prepared by a method comprising the steps of:

collating and combining selected chemical constituents in powder form in a first container, the constituents including selected nutrients;

mixing the constituents so as to produce a mixture of constituent particles in powder from;

reducing the size of the mixture constituent particles to nano scale;

cooling the mixture and allowing it to stand in a motionless, unagitated state;

combining and mixing the mixture with sealing ingredients;

allowing the combination of the sealing ingredient mixture to stand in a motionless, unagitated state so as to effect liquid sealing and a first bonding of the constituents; combining and mixing the sealed and first bonded mixture with a selected volume of purified H2O, and allowing it to stand in a motionless, unagitated state so as to enable the physical state of the mixed sealing ingredients to transform from relatively solid nano powder from to a relatively thick clear nano liquid form, whereupon completion generally of the physical state transformation, a first bonding protective seal of the constituents is finalized, the nano liquid constituents having a size of about 18 nanometers;

sterilizing the first bonding protective sealed mixture and allowing it to stand in a motionless, unagitated state;

combining and mixing selected volumes of H2O between about 7.5 PH and 9.5 PH, saline Aptms, and oleic acid with the sterilized first bonding protective sealed mixture;

freezing the mixed combination of H2O, saline, oleic acid and protective sealed mixture so as to effect relatively permanent second bonding of the constituents of the protective sealed mixture to interior and/or exterior layers of the H2O molecule;

thawing the mixed combination so as to form a nano solid liquid water concentrate of constituents; and combining and mixing the nano solid liquid water concentrate with selected volumes of mesoporous silica and oleic acid so as to stabilize and provide sealing protection to the protective sealed mixture bonded to the exterior layer of the H2O molecule, such that the nano liquid constituents have a size generally within a range of 12 and 16 nanometers, and the protective sealed mixture bonded to the interior and/or exterior layers of the H2O molecule has a stability of approximately 100%.

In accordance with another aspect of the disclosure, a colored, fragrant and/or flavored concentrate containing molecules of H2O is provided, each encapsulating a composite nano particle including selected nutrients, the concentrate prepared by a method comprising the steps of:

collating and combining selected chemical constituents in powder form in a first container, the constituents including selected nutrients;

mixing the constituents so as to produce a mixture of constituent particles in powder form;

reducing the size of the mixture constituent particles to nano scale;

cooling the mixture and allowing it to stand in a motionless, unagitated state;

combining and mixing the mixture with sealing ingredients;

allowing the combination of the sealing ingredient mixture to stand in a motionless, unagitated state so as to effect liquid sealing and a first bonding of the constituents;

combining and mixing the sealed and first bonded mixture with a selected volume of purified H2O, and allowing it to stand in a motionless, unagitated state so as to enable the physical state of the mixed sealing ingredients to transform from relatively solid nano powder form to a relatively thick clear nano liquid form, whereupon completion generally of the physical state transformation, a first bonding protective seal of the constituents is finalized, the nano liquid constituents having a size of about 18 nanometers;

sterilizing the first bonding protective sealed mixture and allowing it to stand in a motionless, unagitated state;

injection molding the sterilized first bonding protective sealed mixture so as to achieve particle injection;

combining and mixing selected volumes of H2O between about 7.5 PH and 9.5 PH, saline Aptms, and oleic acid with the particle injected, sterilized first bonding protective sealed mixture;

freezing the mixed combination of H2O, saline, oleic acid and protective sealed mixture so as to effect relatively permanent second bonding of the constituents of the protective sealed mixture to interior and/or exterior layers of the H2O molecule;

thawing the mixed combination so as to form a nano solid liquid water concentrate of constituents; and combining and mixing the nano solid liquid water concentrate with selected volumes of mesoporous silica and oleic acid so as to stabilize and provide sealing protection to the protective sealed mixture bonded to the exterior layer of the H2O molecule, such that the nano liquid constituents have a size generally within a range of 12 and 16 nanometers, and the protective sealed mixture bonded to the interior and/or exterior layers of the H2O molecule has a stability of approximately 100%.

According to still another aspect of the disclosure, there is provided a method of treatment using a nano nutraceutical composition. The method comprises the steps of: preparing a stabilized and sealed nano solid liquid H2O concentrate comprising a protective sealed mixture bonded to interior and/or exterior layers of H2O molecules, such that the nano liquid constituents have a size generally within a range of 12 and 16 nanometers, and the protective sealed mixture has a stability of approximately 100%; blending about a first selected volume of the stabilized and sealed nano solid liquid water concentrate with a second selected volume of filtered bottled H2O, so as to produce a colorless, odorless, tasteless nano vitamin beverage; and dispensing to a patient a selected daily dosage of the vitamin beverage in the amount of at least 1 liter.

It is, therefore, an object of this disclosure to provide a multi-component nutritional delivery system that can be incorporated into beverages, food products, medical products, pharmaceuticals, oral care products and the like through effective encapsulation of one or multiple active ingredient(s) and release of the ingredient(s) in a manner suitable for effective absorption into a user's body.

Another object of the disclosure is to provide a delivery system that enhances the stability and bioavailability of a wide range of nutraceutical ingredients, prolongs their residence time in the body to insure adequate absorption, and optimizes their health benefits.

It is a further object of the disclosure to provide an efficient and economical delivery system for nutritional compounds and associated single component and/or complex compounded ingredients, whether water-soluble or water-insoluble and whether oil-soluble or oil-insoluble.

Still another object of the disclosure is to provide a nutritional supplement that is relatively easy to administer, excludes potentially harmful compounds, and eliminates the ingestion of unnecessary vitamins as well as other unnecessary substances and additives characteristic of conventional nutritional supplements.

Yet another object of the disclosure is to provide an efficient and economical process for incorporating nutraceuticals in food products and beverages by effectively encapsulating one or multiple active ingredients, enhancing their stability and bioavailability, controlling their release characteristics, and optimizing their bioabsorption into the body during food product and/or beverage consumption.

Still a further object of the disclosure is to provide a stable nutraceutical composition and method that not only includes key nutritional constituents, but is also affordable, readily manufacturable, and easily made available in concentrations that are highly effective for improving the overall health, comfort, vitality, well being, strength and stamina of users.

Yet a further object of the disclosure is to provide a tasteless, colorless and odorless nutraceutical composition that fully and stably disperses in aqueous media for use in food and beverage compositions and the like.

Another object of the disclosure is to provide an efficient and economical composition and method for effecting stable disbursement of one or more nutraceuticals in a water soluble medium without the taste, color and/or odors associated with conventional compositions.

Still another object of the disclosure is to provide an improved system for delivery of nutraceuticals to users.

It is a further object of the disclosure is to utilize nano technology to provide for quick, convenient, stable and effective delivery of nutraceuticals.

Another object of the disclosure is to provide a nutritional supplement that is highly effective for improving the overall health, comfort, vitality and well being of patients under treatment in hospitals and others in need of nutritional aid.

It is a yet another object of the disclosure is to provide a nutritional supplement particularly well suited for people generally in their later years of life.

Still another object of the disclosure is to provide a nutritional supplement that is not only suitable for health maintenance of athletes, but is also appropriate for pregnant women as well as highly active professionals in need of additional nutrition.

Yet another object of the disclosure is to counteract the considerably lower energy levels and fatigue suffered by patients during hospitalization.

Another object of the disclosure is to provide an enhanced nutritional supplement and method of treatment using the same that is efficient, effective and economical.

Yet a further object of the disclosure is to provide a novel nutritional supplement in bottled water form comprising vitamin C and B vitamins for improving the overall health, comfort, vitality, well being, strength and stamina of a user.

Another object of the disclosure is to provide a novel nutritional supplement in a concentrate for reconstitution, nutritional bar or other food comprising a nano nutraceutical composition for improving the overall health, comfort, vitality, well being, strength and stamina of a user.

Yet another object of the disclosure is to provide a nutritional supplement for preventing and/or countering the effects of Alzheimer's Disease, Chronic Fatigue Syndrome (CFS), Chronic Muscle Myopathy, Diabetes, Dieting, Epilepsy, Heart Disease, Immune Deficiency, Muscle Atrophy, Old Age, and Stroke, where CBD (cannabidiol) is such an example due to the plurality of medical research studies showing CBD prevents and/or counters the effects of Diabetes, Epilepsy and Heart Disease.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
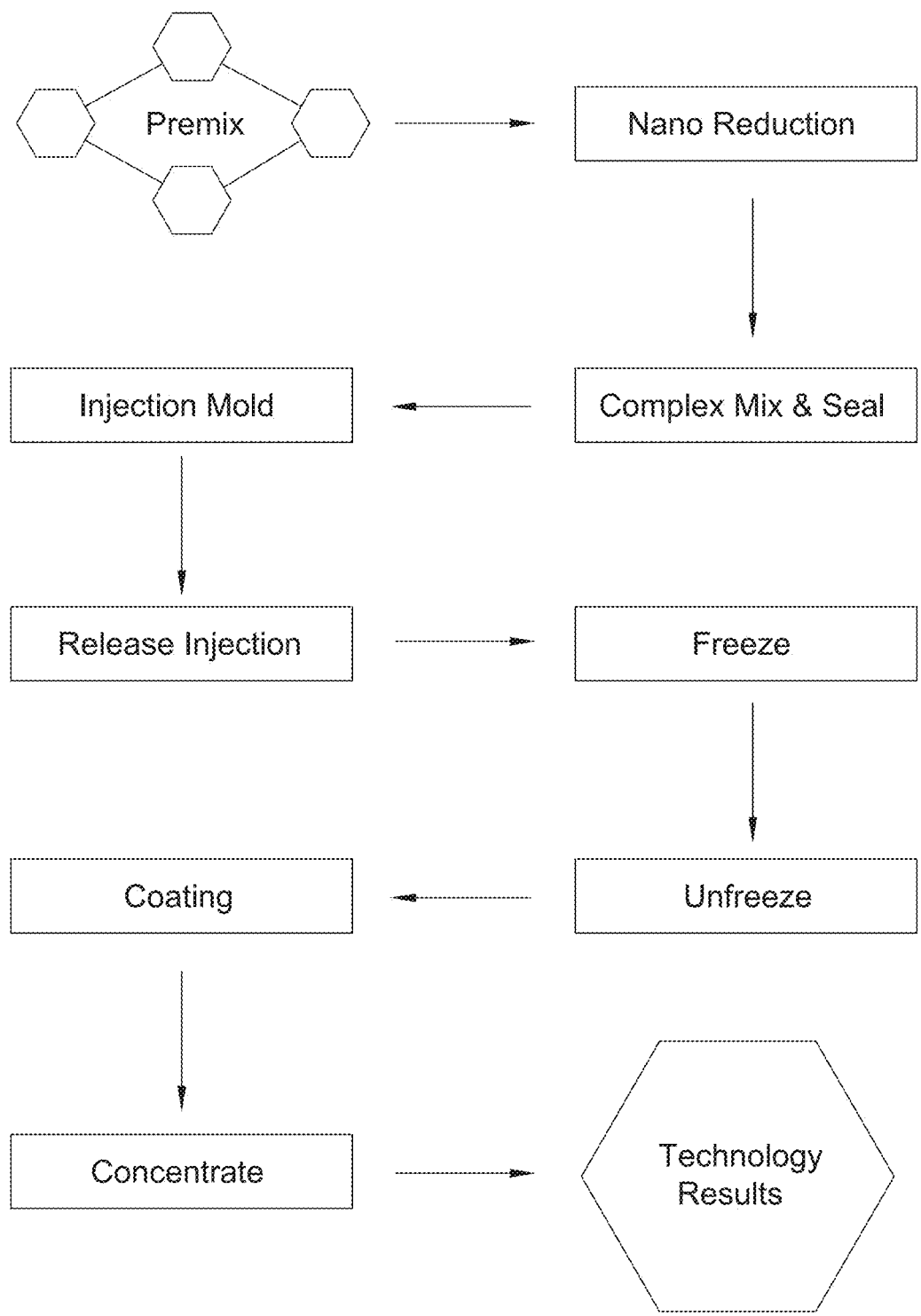
FIG. 1 is a flow diagram illustrating schematically steps for preparation of a nano nutraceutical composition, including optional injection steps, in accordance with various aspects of the disclosure.

Still other objects and advantages of the disclosure will become apparent from the following description.

DETAILED DESCRIPTION

One of the most important nutrients for maintaining good health and well-being of humans is vitamin C. It plays a key role as a component of enzymes involved in the natural synthesis, biotransformation and bioabsorption of proteins in the body. Possibly the most important role of vitamin C is in the maintenance of a healthy immune system. Specifically, vitamin C stimulates the immune system and protects against damage by free radicals released by the body in its fight against infection.

Medical research has shown that people who suffer from asthma, arthritis, cancer, diabetes, and heart disease have much lower levels of vitamin C in their blood than do healthy people. It has also been determined that vitamin C supplements significantly lower the risk of cataracts and glaucoma. Further, vitamin C deficiency, in turn, results in increased risk of skin breakdown, prolonged wound healing time, decreased response to and, hence, prolonged duration of infection, iron-deficiency anemia, bleeding gums and other dental problems.

Turning now to B vitamins, they are a class of water-soluble nutrients that play important roles in cell metabolism. Research shows that each B vitamin is a nutrient compound chemically distinct from the others. Traditional nutritional supplements containing all eight are referred to as a vitamin B complex.

Generally speaking, each B vitamin is either a cofactor for key metabolic processes or is a precursor needed to make one. Notably, vitamin B1 (also known as thiamine) plays a central role in the generation of energy from carbohydrates. It is involved in RNA and DNA production, as well as nerve function. Vitamin B5 (or pantothenic acid) is involved in the oxidation of fatty acids and carbohydrates. Coenzyme A, which can be synthesised from pantothenic acid, is involved in the synthesis of amino acids, fatty acids, ketones, cholesterol, [5] phospholipids, steroid hormones, neurotransmitters (such as acetylcholine), and antibodies. Vitamin B6 (the active form of which is known as pyridoxal 5'-phosphate) serves as a cofactor in many enzyme reactions mainly in amino acid metabolism including biosynthesis of neurotransmitters. As for vitamin B12 (or methylcobalamine), this nutrient is involved in the cellular metabolism of carbohydrates, proteins and lipids. It is considered essential for the production of blood cells in bone marrow, and for nerve sheaths and proteins.

Deficiencies in B vitamins can lead to a wide range of health problems. Vitamin B 1 deficiency, for example, has been known to cause beriberi, weakness and pain in the limbs, irregular heartbeat, and even dementia. Deficiency in vitamin B5 can cause acne or tickling or burning sensations in the skin. Inadequate vitamin B6 consumption has been linked to seborrhoeic dermatitis, pink eye, and epilepsy. Shortfalls in vitamin B12 has led to macrocytic anemia, peripheral neuropathy, memory loss and other cognitive deficits.

Dr. Rodger Adams, a chemist who graduated from Harvard University, and his team at the University of Illinois were the first to successfully extract CBD (cannabidiol) from the *Cannabis sativa* plant. CBD is a phytocannabinoid, where phytocannabinoids refers to any cannabinoid that is naturally occurring within the *Cannabis* family of plants. CBD is directly derived from the hemp plant.

Since the discovery of CBD (cannabidiol), people have been exploring possible uses and benefits. Through these explorations and studies of CBD, benefits have been found and many possible further benefits of CBD are currently being pursued. Below is just a small listing of the benefits of CBD that has been found through research studies.

From the many research studies, CBD was able to reduce the number of seizures, especially child seizures, and in some cases, CBD was able to stop them altogether. Also, several studies have shown that regular *Cannabis* users have a reduced risk of diabetes and obesity. Other studies have found that current *Cannabis* users compared to non-*Cannabis* users and former *Cannabis* users had higher blood levels of high-density lipoprotein (HDL-C), the so-called good cholesterol. Another study found regular *Cannabis* users had increased levels of high-density lipoprotein and slightly lower levels of low-density lipoprotein (LDL-C), the so-called bad cholesterol. Additionally, there are a myriad of studies where CBD (cannabidiol) has been used for successful pain management.

One remarked able aspect of CBD (cannabidiol) is the lack of health problems. A report from the World Health Organization states "In humans, CBD exhibits no effects indicative of any abuse or dependence potential. . . . To date, there is no evidence of public health related problems associated with the use of pure CBD".

One last study has shown that CBD is completely safe to consume in foods and drinks and is considered to be non-toxic. From the plurality of health benefits as well as CBD being safe to consume, both in foods and drinks, CBD (cannabidiol) is one example of a nutritional supplement of this invention.

The foregoing description is provided for purposes of illustration and not to limit the intended content or application of the present invention. The remaining aspects of the structure, function and chemistry of the foregoing are considered known by those skilled in the art and further description is considered unnecessary for illustration of the composition disclosed herein.

Referring now to the disclosure and, more particularly, to FIGS. 1-7, an advanced nano nutraceutical composition and method is provided and, according to one embodiment, a colorless, odorless, tasteless molecule of H2O encapsulating a composite nano particle, the composite particle including selected nutrient particles of nano scale. At the kernel of the present invention is a relatively high concentration of nutrients, notably, vitamin C and B vitamins. The composite nano particle preferably includes selected vitamin particles of nano scale including, but not limited to, vitamin C (sodium ascorbate), vitamin B1 (thiomine), vitamin B5 (pantothenic acid), vitamin B6 (pyridoxine), and vitamin B12 (methylcobalamine).

Alternatively, a nutritional supplement, such as CBD, is provided which a colored, fragrant and/or flavored molecule of H2O encapsulating a composite nano particle, the composite particle including selected nutrient particles of nano scale including, but not limited to, sodium ascorbate, methylcobalamine, pyridoxine, thiomine and pantothenic acid.

In use, the nano nutraceutical compositions disclosed are preferably produced as a nano solid liquid H2O concentrate containing molecules of H2O, each encapsulating a composite nano particle including selected nutrient particles of nano scale. Desirably, the composite particles each have a size generally within a range of 12 nanometers and 16 nanometers, and a bond between the composite particles and respective interior and/or exterior layers of the H2O molecule that is stabilized and sealed, the seal having a stability of approximately 100%. Also, it is considered desirable that between about 100 and about 200 composite nano particles are bonded, stabilized and sealed about each water molecule.

Alternatively or concurrently, the concentrate is readily mixed with and/or dissolved in bottled water so as to produce a flavorless, colorless, tasteless, odorless nano vitamin water, in particular, a nano solid liquid H2O beverage containing the molecules of H2O encapsulating a composite nano particle including selected nutrient particles of nano scale. As above, the composite particles each have a size generally within a range of 12 nanometers and 16 nanometers, and a bond between the composite particles and respective interior and/or exterior layers of the H2O molecule that is stabilized and sealed, the seal having a stability of approximately 100%. Further in the alternative, the concentrate may include coloring, fragrant and/or flavoring ingredient s, within the spirit and scope of this disclosure.

Also at the kernel of this disclosure is a method of preparing the nano solid liquid H2O concentrate and, more specifically, a colorless, odorless, tasteless concentrate containing molecules of H2O each encapsulating a composite nano particle including selected nutrients. The method, shown schematically in FIG. 1, includes, but is not limited to, the steps described in detail below.

First, the selected chemical constituents provided in powder form are collated and combined in a first container, e.g., a 2 gallon container or jug, the constituents including selected nutrients. As described above, though not to limit this disclosure to what is described herein, the nutrients preferably include one or more vitamins, for example, sodium ascorbate (vitamin C), methylcobalamine (vitamin B12), pyridoxine (vitamin B6), thiomine (vitamin B1) and/ or pantothenic acid (vitamin B5). Suitable quantities and/or proportions of the respective nutrients, by one example, include, but are not limited to, approximately 1 lb powder weight of sodium ascorbate, about 0.25 lb powder weight of thiamine, approximately 1.50 lbs powder weight of pantothenic acid, roughly 0.50 lb powder weight of pyridoxine, and around 1 lb powder weight of methylcobalamine.

Figure 2:
FIG. 2 shows photographically a first premix of chemical constituents, according to one aspect of the disclosure.

The constituents are then mixed, e.g., using a conventional magnetic stirring device, in the first container for approximately 1 minute at ambient pressure and a temperature generally within a range of 70° F. and 75° F. so as to produce a first premix of constituent particles in powder form. As illustrated in FIG. 2, the resulting premix, according to one arrangement, is a white colored powder having a generally chalky flavor. At this initial stage of production, all of the constituents including nutrients are considered officially to be mixed together.

Next, the nano reduction process is performed. For instance, the first premix is transferred from the first container to a suitably sized chamber of an apparatus, e.g., a conventional, non-ultrasonic nano emulsion mill production machine, for mechanically reducing the size of the constituent particles to nano scale. The size reduction apparatus is set and operated, by traditional operating procedures, so as to produce a second premix comprising a nano emulsion of constituent particles between about 6 nanometers and about 20 nanometers in size.

After size reduction apparatus operation has been completed, the second premix is transferred to a nano cooling apparatus, such as a conventional nano cooling system. The second premix is cooled in the nano cooling apparatus for between about 10 minutes and about 30 minutes at ambient pressure, at a temperature generally within a range of 7° C. and 12° C. Once nano cooling has concluded, the second premix is desirably transferred to a new or second container, e.g., a 2 gallon container or jug. At this point, the process of nano particle size reduction is considered complete.

Thereafter, a complex mix and seal stage is performed. More particularly, a plurality of sealing ingredients are collated and combined in a third container, e.g., a 3 gallon container or jug, the ingredients including a selected antisolvent, such as crystallization sodium oleate and tetra methylammonium-dodeyclamine, each in liquid form and in measured amounts of between about 500 ml and about 700 ml. The sealing ingredients are mixed mechanically, e.g., using a conventional magnetic stirring device, for approximately 1 minute, and then allowed to remain stationary, e.g., in a motionless, unagitated state, for between about 10 minutes to about 15 minutes at ambient temperature and pressure.

Subsequently, the mixed sealing ingredients, i.e., mixture of 3 liquid ingredients are desirably transferred to a fourth container, e.g., a 5 gallon container or jug, and, in turn, the second premix from the second container are collated and combined in the fourth container in and with the mixed sealing ingredients from the third container. The combination of the second premix and mixed sealing ingredients in the fourth container are then allowed to remain stationary, i.e., in a motionless and unagitated state, and without influence from electrical shock, for between about 20 minutes and about 40 minutes at ambient pressure, and a temperature generally within a range of 60° F. and 80° F., so as to effect liquid sealing and a first bonding of the constituents.

Next, about 1 liter of H2O purified by reverse osmosis is collated and combined with the sealed and first bonded combination of the second premix and mixed sealing ingredients in the fourth container. The purified H2O is then mixed (e.g., stirred using a conventional magnetic stirring device) with the sealed and first bonded combination of the second premix and mixed sealing ingredients for approximately 1 minute.

Thereafter, the mixed purified H2O and sealed and first bonded combination are allowed to remain stationary, i.e., in a motionless, unagitated state, for between about 30 minutes and about 60 minutes at ambient temperature and pressure. This enables the physical state of the mixed sealing ingredients to transform from relatively solid nano powder form to a relatively thick clear nano liquid form, whereupon completion generally of the physical state transformation, a first bonding protective seal of the constituents is finalized. At this stage, the nano liquid constituents have a size of about 18 nanometers.

Subsequently, the finalized first bonding protective sealed mixture of purified H2O and sealed and first bonded combination is transferred, e.g., poured, into a sterilization apparatus, such as conventional sterilization homogenization equipment, to sterilize all of the constituents. The apparatus is activated, and the first bonding protective sealed mixture is sterilized. After sterilization has been completed, the sterilized first bonding protective sealed mixture is allowed to remain stationary, i.e., in a motionless, unagitated state, for between about 20 minutes and about 40 minutes at ambient temperature and pressure; preferably or, in the alternative, optionally after the constituents are re-nano formulated and bonded in a clear liquid mold coating.

At this stage of processing, it is considered desirable that a sample be taken of the sterilized first bonding protective sealed mixture or nano liquid, e.g., between about 5 ml and about 10 ml, and tested for stability and constituent nano particle size. Preferably, precision testing is conducted using a conventional nano analyzer machine. Suitably, the test yields particle size results of about 18 nanometers, and a stability of approximately 100%. Also, it is noted that, at this stage, the nano liquid is colorless, odorless and flavorless.

After sterilization has been completed, and in preparation for the freezing step, the contents of the sterilization apparatus, i.e., the sterilized first bonding protective sealed mixture is transferred to, e.g., poured into, a fifth container, e.g., a 10 gallon container or jug. The sterilized first bonding protective sealed mixture in the fifth container is, in turn, collated and combined with: H2O, e.g., about 3.785 liters, having a PH generally within a range of 7.5 and 9.5; saline, e.g., 3-aminopropyltrimethoxysilane (saline Aptms), e.g., in a volume of between about 200 ml and 250 ml; and oleic acid in a dry or liquid format, e.g., in a liquid format having a volume of between about 200 ml and 250 ml. The respective volumes of saline Aptms and oleic acid, it is preferred, are delivered in equivalent amounts such as 250 ml each. The combination of H2O, saline, oleic acid and protective sealed mixture is then mixed, e.g., stirred using a conventional magnetic stirring device, for between about 15 minutes to about 30 minutes.

Generally speaking, the freezing bonding process is considered to be the most important liquid nano beverage format step. According to one arrangement, the fifth container containing the mixed combination of H2O, saline, oleic acid and protective sealed mixture is placed in a conventional walk-in freezer at ambient pressure, and at a temperature generally within a range of 25° F. and 32° F., then allowed to freeze for between about 3 hours to about 4 hours. This effects relatively permanent second bonding of the constituents of the protective sealed mixture to interior and/or exterior layers of the H2O molecule.

Figure 3:
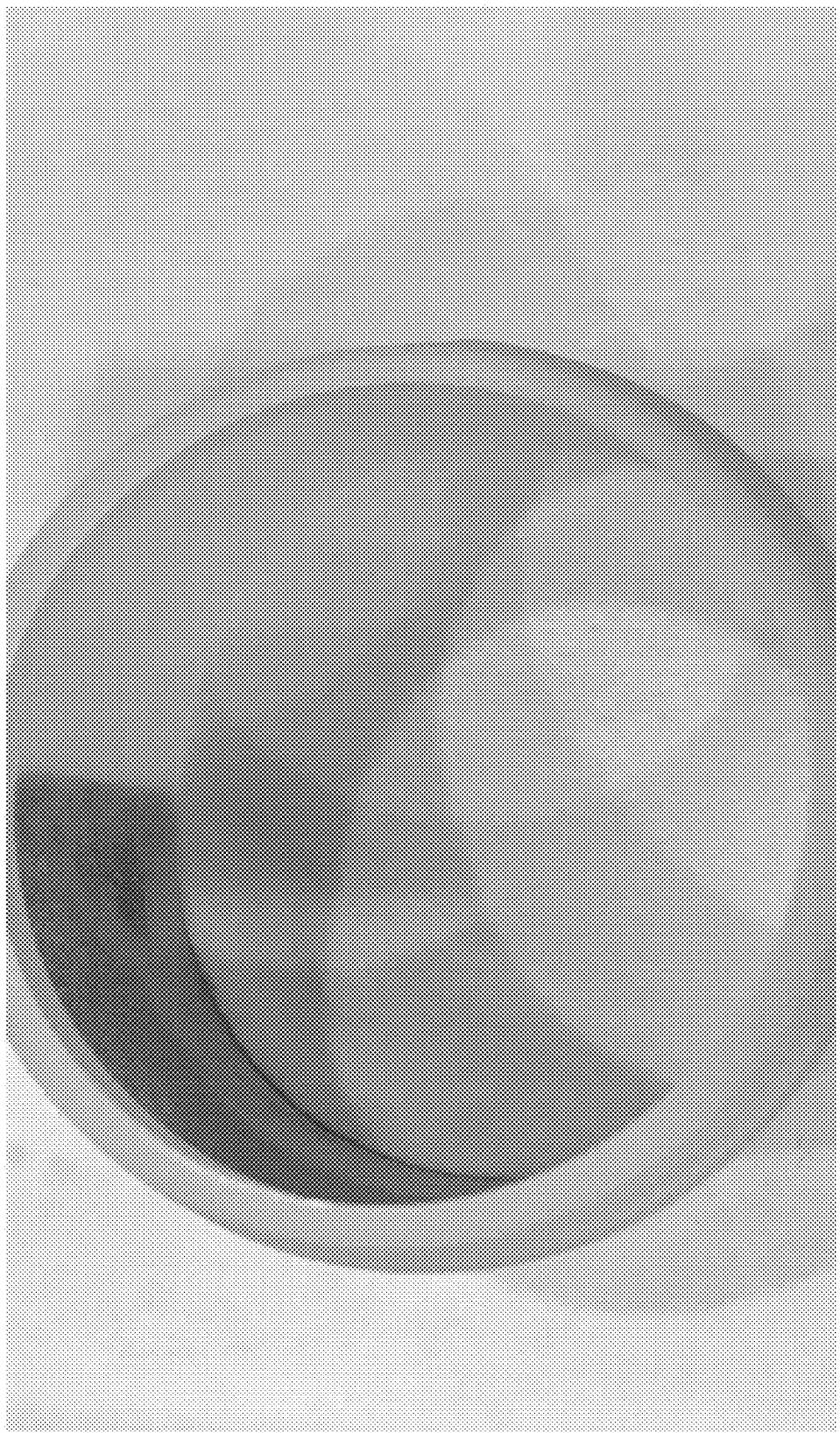
FIG. 3 illustrates photographically a raw nano concentrate prepared from the constituents shown in FIG. 2, after the freezing step of the nano bonding process.

Thereafter, the contents of the fifth container are removed from the walk-in freezer and allowed to sit out and thaw for about 4 hours to about 5 hours at ambient temperature and pressure, such that the contents become one, nano solid liquid H2O concentrate containing all of the constituents, i.e., nutrients and ingredients that are colorless, odorless and tasteless. A concentrate of this general description is shown in FIG. 3.

Next, an additional coating step is performed. Briefly, the nano solid liquid H2O concentrate is reapplied into a powdered form in a dry format by being collated and combined with about 500 ml of mesoporous silica and about 500 ml of a surfactant, e.g., oleic acid. The combination of nano solid liquid water concentrate, mesoporous silica and oleic acid are then mixed, e.g., stirred using a conventional magnetic stirring device, at ambient pressure and temperature for up to about 2 minutes. This stabilizes and seals the exterior layer of the H2O molecule. In other words, it provides sealing protection to the protective sealed mixture bonded to the exterior layer of the H2O molecule, such that the nano liquid constituents have a size generally within a range of 12 nanometers and 16 nanometers, and the protective sealed mixture bonded to the interior and/or exterior layers of the H2O molecule has a stability of approximately 100%.

At this point, it is preferred that the concentrate again be tested to verify stability and nano particle size. Using a conventional nano analyzer machine, a sample of the concentrate is taken and tested. The test results confirm that the nano particle size of the constituents is between about 12 nanometers and about 16 nanometers, and that the stability of the H2O molecule with composite nano particle ingredients and nutrients along with vitamins were stabilized at about 100%. Upon inspection, the concentrate is colorless, ordorless and tasteless.

Subsequently, it is further desired that the concentrate formulation be tested for performance. First, a sample is taken, e.g., about 5 ml, of the current concentrate or nano finished raw concentrate. Second, the sample is combined with about 28.8 fluid ounces of filtered H2O in a 1 liter (33.8 fluid ounces) bottle. Third, the combined sample and H2O is blended, e.g., shaken or stirred using a conventional magnetic stirring device, inside the bottle. Fourth, the blended combination of sample and H2O are tested, e.g., using a conventional gas chromatograph or the like, to determine and confirm the presence and amount in percentage of each individual nutrient, i.e., vitamin, based on a recommended daily intake (RDA). This generally equals the daily nutritional requirements based on a 2000 calorie diet.

Figure 4:
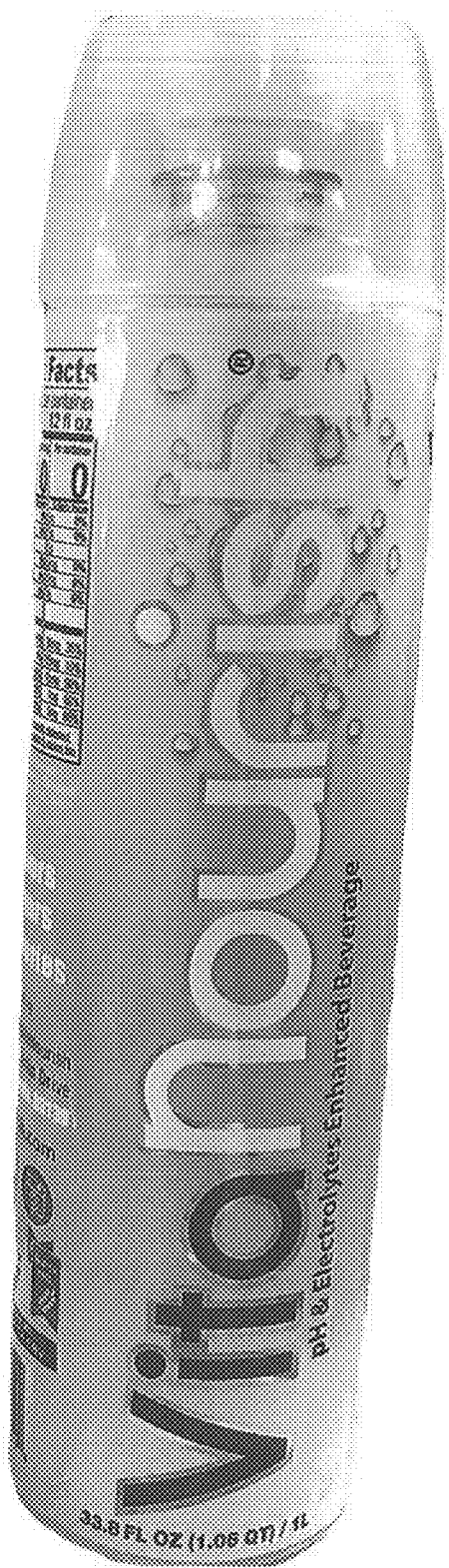
FIG. 4 shows the finished nano concentrate disbursed in a nano vitamin H2O product in accordance with the constituents set forth in FIG. 2.
Figure 5:
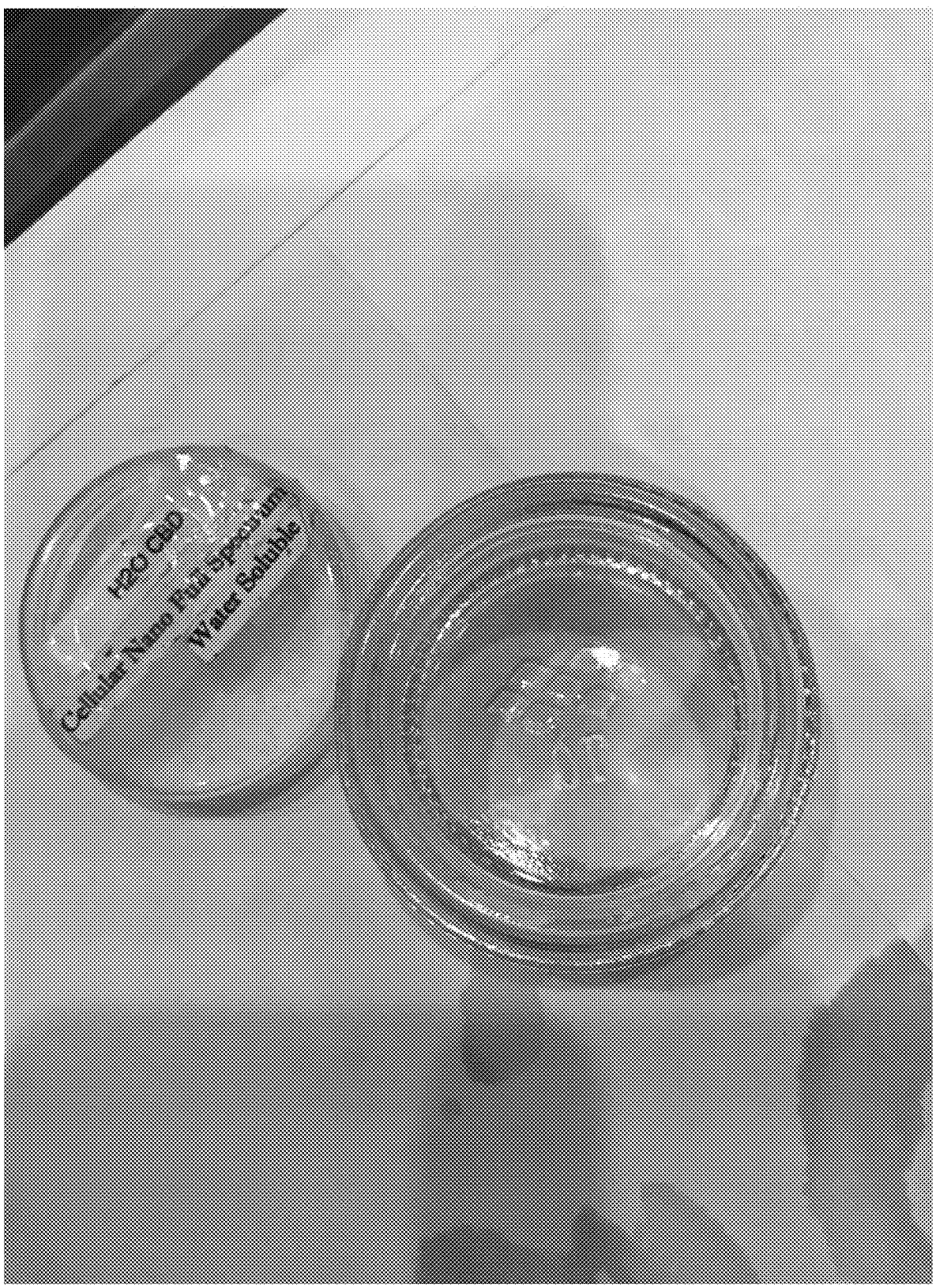
FIG. 5 illustrates photographically liquid water encapsulating CBD.
Figure 6:
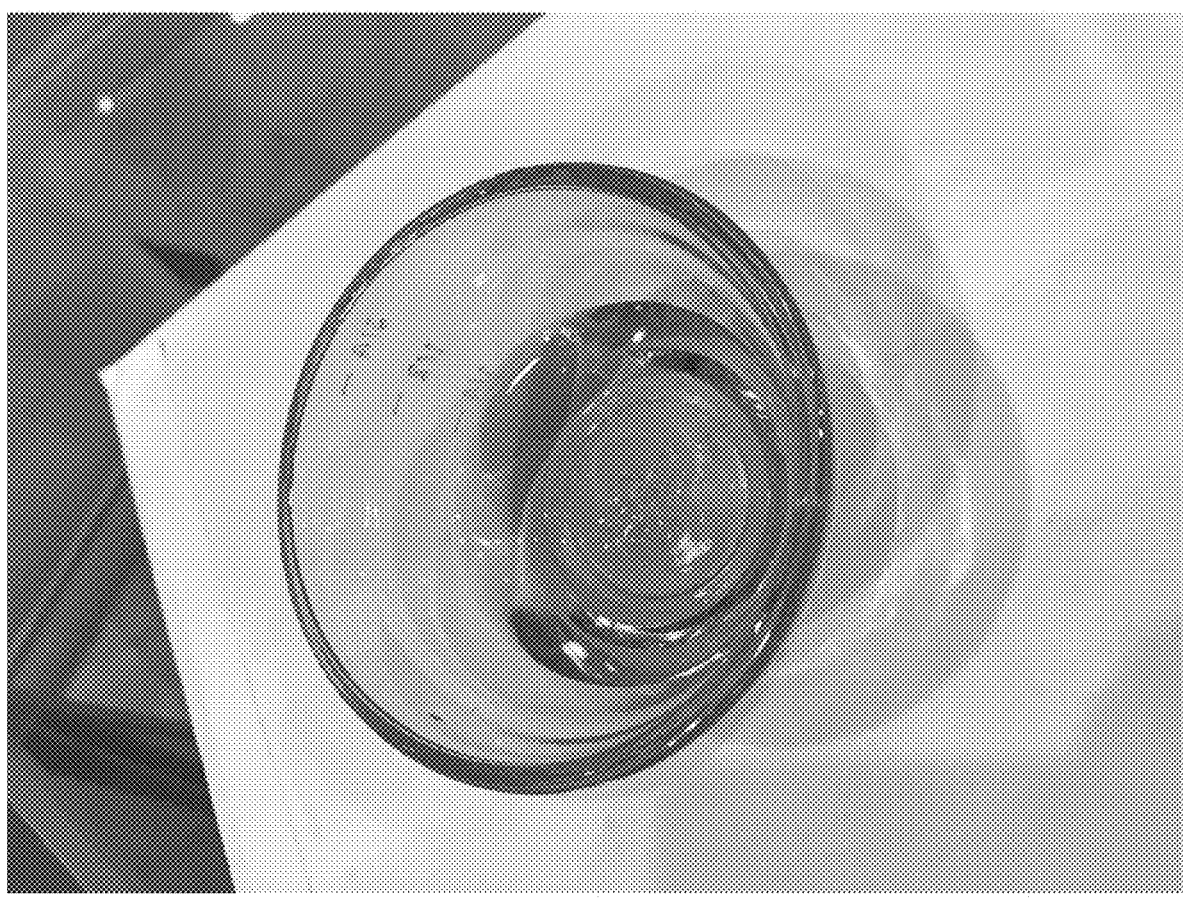
FIG. 6 illustrates photographically colored liquid water encapsulating a composite nano particle.
Figure 7:
FIG. 7 illustrates photographically liquid water encapsulating a composite nano particle.

The composition performance tested above, involving blending about 5 ml of the stabilized and sealed nano solid liquid water concentrate with about 1 liter of filtered bottled H2O, is also considered a preferred embodiment of this disclosure. As illustrated in FIG. 4, the blended combination is a colorless, odorless, flavorless nano vitamin H2O product for distribution and sale.

Optionally, the nano analyzer is used to test the amount of nano sized conversion performed from a powder vitamin format and that amount not converted and transferred over to the nano sized water molecule, between about 14 nanometers and about 16 nanometers, of this disclosure.

Although the nano finished raw concentrate produced by the above-described method is shown and described for combination with H2O to produce a nano vitamin H2O product, its application via concentrate and/or nano sized water molecules to other consumables and/or non-consumables is understood, given consideration to the purpose for which the concentrate and method are intended. For example, application through appropriate nutrients to food engineering including water and oil based compositions, plants in agricultural and gardening contexts, pharmaceutical delivery systems as well as medical applications are within the spirit and scope of this disclosure.

Turning now to another aspect of the disclosure, there is provided a colored, fragrant and/or flavored concentrate containing molecules of H2O each encapsulating a composite nano particle including selected nutrients, e.g., vitamins. The concentrate is prepared by the method illustrated in FIG. 1, which comprises a series of exemplary steps, this time including injection mold and injection release, as described in detail below.

As before, the selected chemical constituents provided in powder form are initially collated and combined in a first container, e.g., a 2 gallon container or jug, the constituents including selected nutrients. While not intended to limit this disclosure to what is described herein, the nutrients preferably include one or more vitamins, for example, sodium ascorbate (vitamin C), methylcobalamine (vitamin B12), pyridoxine (vitamin B6), thiomine (vitamin B1) and/or pantothenic acid (vitamin B5) as well as strong nutrient agents have a superior flavor and color profile. Suitable quantities and/or proportions of the respective nutrients, by one example, include, but are not limited to, approximately 1 lb powder weight of sodium ascorbate, about 0.25 lb powder weight of thiamine, approximately 1.50 lbs powder weight of pantothenic acid, roughly 0.50 lb powder weight of pyridoxine, and around 1 lb powder weight of methylcobalamine.

The constituents are then mixed, e.g., using a conventional magnetic stirring device, in the first container for approximately 1 minute at ambient pressure and a temperature generally within a range of 70° F. and 75° F. so as to produce a first premix of constituent particles in powder form. The resulting premix, according to one embodiment, is a colored powder having a flavor corresponding to the strong nutrient agent(s) utilized. At this initial stage of production, all of the constituents including nutrients are considered officially mixed together.

Next, the nano reduction process is performed. For instance, the first premix is transferred from the first container to a suitably sized chamber of an apparatus, e.g., a conventional, non-ultrasonic nano emulsion mill production machine, for mechanically reducing the size of the constituent particles to nano scale. The size reduction apparatus is set and operated by traditional means so as to produce a second premix comprising a nano emulsion of constituent particles between about 6 nanometers and about 20 nanometers in size.

After size reduction apparatus operation has been completed, the second premix is transferred to a nano cooling apparatus, such as a conventional nano cooling system. The second premix is cooled in the nano cooling apparatus for between about 10 minutes and about 30 minutes at ambient pressure, at a temperature generally within a range of 7° C. and 12° C. Once nano cooling has concluded, the second premix is desirably transferred to a new or second container, e.g., a 2 gallon container or jug. At this point, the process of nano particle size reduction is considered complete.

Thereafter, and as before, a complex mix and seal stage is performed. More particularly, a plurality of sealing ingredients are collated and combined in a third container, e.g., a 3 gallon container or jug, the ingredients including a selected anti-solvent, such as crystallization sodium oleate and tetra methlyrummonium-dodeyclamine, each in liquid form and in measured amounts of between about 500 ml and about 700 ml. The sealing ingredients are mixed mechanically, e.g., using a conventional magnetic stirring device, for approximately 1 minute, and then allowed to remain stationary, e.g., in a motionless, unagitated state, for between about 10 minutes to about 15 minutes at ambient temperature and pressure.

Subsequently, the mixed sealing ingredients, i.e., mixture of 3 liquid ingredients, are desirably transferred to a fourth container, e.g., a 5 gallon container or jug, and, in turn, the second premix from the second container is collated and combined in the fourth container in and with the mixed sealing ingredients from the third container. The combination of the second premix and mixed sealing ingredients in the fourth container are then allowed to remain stationary, i.e., in a motionless and unagitated state, and without influence from electrical shock, for between about 20 minutes and about 40 minutes at ambient pressure, and a temperature generally within a range of 60° F. and 80° F., so as to effect liquid sealing and a first bonding of the constituents.

Next, about 1 liter of $H_2O$ purified by reverse osmosis is collated and combined with the sealed and first bonded combination of the second premix and mixed sealing ingredients in the fourth container. The purified $H_2O$ is then mixed (e.g., stirred using a conventional magnetic stirring device) with the sealed and first bonded combination of the second premix and mixed sealing ingredients for approximately 1 minute.

Thereafter, the mixed purified $H_2O$ and sealed and first bonded combination is allowed to remain stationary, i.e., in a motionless, unagitated state, for between about 30 minutes and about 60 minutes at ambient temperature and pressure. This enables the physical state of the mixed sealing ingredients to transform from relatively solid nano powder form to a relatively thick clear nano liquid form, whereupon completion generally of the physical state transformation, a first bonding protective seal of the constituents is finalized. At this stage, the nano liquid constituents have a size of about 18 nanometers.

Subsequently, the finalized first bonding protective sealed mixture of purified $H_2O$ and sealed and first bonded combination is transferred, e.g., poured, into a sterilization apparatus, such as conventional sterilization homogenization equipment, to sterilize all of the constituents, the apparatus is activated, and the first bonding protective sealed mixture is sterilized. After sterilization has been completed, the sterilized first bonding protective sealed mixture is allowed to remain stationary, i.e., in a motionless, unagitated state, for between about 20 minutes and about 40 minutes at ambient temperature and pressure; preferably or, in the alternative, optionally after the constituents are re-nano formulated and bonded in a clear liquid mold coating.

At this stage of processing, it is considered desirable that a sample be taken of the sterilized first bonding protective sealed mixture or nano liquid, e.g., between about 5 ml and about 10 ml, and tested for stability and constituent nano particle size. Preferably, precision testing is conducted using a conventional nano analyzer machine. Suitably, the test yields particle size results of about 18 nanometers, and a stability of approximately 100%. Also, it is noted that the nano liquid is colored and flavored. After sterilization has been completed, the sterilized first bonding protective sealed mixture is subjected to an injection mold so as to achieve particle injection, and then a nano release injection step, to insure particle bonding. It is understood that particle injection and nano release are generally necessary where the nano liquid is flavored, fragrant and/or colored such as when there are strong nutrient agents that have a superior flavor, fragrance and/or color profile.

In preparation for the freezing step, the contents of the sterilization apparatus, i.e., the particle injected, sterilized first bonding protective sealed mixture, is transferred to a fifth container, e.g., a 10 gallon container or jug. The particle injected, sterilized first bonding protective sealed mixture in the fifth container is, in turn, collated and combined with: $H_2O$, e.g., about 3.785 liters, having a PH generally within a range of 7.5 and 9.5; saline, e.g., 3-aminopropyltrimethoxysilane (saline Aptms), e.g., in a volume of between about 200 ml and 250 ml; and oleic acid in a dry or liquid format, e.g., in a liquid format having a volume of between about 200 ml and 250 ml. The respective volumes of saline Aptms and oleic acid, it is preferred, are delivered in equivalent amounts such as 250 ml each. The combination of $H_2O$, saline, oleic acid and protective sealed mixture is then mixed, e.g., stirred using a conventional magnetic stirring device, for between about 15 minutes to about 30 minutes.

In general, the freezing bonding process is deemed to be the most important liquid nano beverage format process. According to one aspect, the fifth container containing the mixed combination of $H_2O$, saline, oleic acid and protective sealed mixture is placed in a conventional walk-in freezer at ambient pressure and at a temperature generally within a range of 25° F. and 32° F., then allowed to freeze for between about 3 hours to about 4 hours. This effects relatively permanent second bonding of the constituents of the protective sealed mixture to interior and/or exterior layers of the $H_2O$ molecule.

Thereafter, the contents of the fifth container are removed from the walk-in freezer and allowed to sit out and thaw for about 4 hours to about 5 hours at ambient temperature and pressure, such that the contents become one, nano solid liquid $H_2O$ concentrate containing all of the constituents, i.e., nutrients and ingredients, that are flavored and colored such as according to strong nutrient constituents selected above.

Next, an additional coating step is performed. Briefly, the nano solid liquid $H_2O$ concentrate is reapplied into a powdered form, i.e., in a dry format, by being collated and combined with about 500 ml of mesoporous silica and about 500 ml of a surfactant, e.g., oleic acid. The combination of nano solid liquid water concentrate, mesoporous silica and oleic acid is then mixed, e.g., stirred using a conventional magnetic stirring device, at ambient pressure and temperature for up to about 2 minutes. This stabilizes and seals the exterior layer of the H2O molecule. In other words, it provides sealing protection to the protective sealed mixture bonded to the exterior layer of the H2O molecule, such that the nano liquid constituents have a size generally within a range of 12 nanometers and 16 nanometers, and the protective sealed mixture bonded to the interior and/or exterior layers of the H2O molecule has a stability of approximately 100%.

At this point, it is considered desirable that the concentrate again be tested to verify stability and nano particle size. Using a conventional nano analyzer machine, a sample of the concentrate is taken and tested. The test results confirm that the nano particle size of the constituents is between about 12 nanometers and about 16 nanometers, and that the stability of the H2O molecule with composite nano particle ingredients and nutrients along with vitamins were stabilized at about 100%. Upon inspection, the concentrate is colored, fragrant and flavored.

Subsequently, it is further desired that the concentrate formulation be tested for performance. First, a sample is taken, e.g., about 5 ml, of the current concentrate or nano finished raw concentrate. Second, the sample is combined with about 28.8 fluid ounces of H2O in a 1 liter (33.8 fluid ounces) bottle. Third, the combined sample and H2O is blended, e.g., shaken or stirred using a conventional magnetic stirring device, inside the bottle. Fourth, the blended combination of sample and H2O are tested, e.g., using a conventional gas chromatograph or the like, to determine and confirm the presence and amount in percentage of each individual nutrient, i.e., vitamin, based on a recommended daily intake (RDA). This generally equals the daily nutritional requirements based on a 2000 calorie diet.

Once again, the composition performance tested above, involving blending about 5 ml of the stabilized and sealed nano solid liquid water concentrate with about 1 liter of filtered bottled H2O, is also considered a preferred embodiment of this disclosure. This time, the blended combination is a colored, fragrant and/or flavored nano vitamin H2O product for distribution and sale. Optionally, use of the nano analyzer is repeated to test the amount of nano sized conversion performed from a powder vitamin format and that amount not converted and transferred over to the nano sized water molecule, between about 14 nanometers and about 16 nanometers, of this disclosure.

As in the case of production of the colorless, odorless, flavorless concentrate, while the nano finished raw concentrate produced by the above method is shown and described for combination with H2O to produce a nano vitamin H2O product, its application via concentrate and/or nano sized water molecule to other consumables and/or non-consumables is understood, given consideration to the purpose for which the concentrate and method are intended.

Referring now to a further aspect of the disclosure, there is provided a method of treatment using a nano nutraceutical composition. By one arrangement, initially stabilized and sealed nano solid liquid H2O concentrate is prepared, the concentrate comprising a protective sealed mixture bonded to interior and/or exterior layers of H2O molecules, such that the nano liquid constituents have a size generally within a range of 12 and 16 nanometers, and the protective sealed mixture has a stability of approximately 100%.

Next, a first selected volume of the stabilized and sealed nano solid liquid water concentrate is blended with a second selected volume of filtered bottled H2O, so as to produce a colorless, odorless, tasteless nano vitamin beverage. The beverage is then dispensed to a patient as a selected daily dosage via the vitamin beverage in the amount of at least 1 liter.

The concentrate of the disclosure may be dispensed in conventional tablet or gel capsule form, in food or a nutritional bar, or in a form for reconstitution, i.e., that may be readily mixed with water or other aqueous-based liquids (e.g., orange juice, grape fruit juice, grape juice, etc.). A further benefit of the present invention is the absence of color, odor and taste. This makes it highly versatile for addition to non-citrus beverages, soups, gravies, sauces and other regular menu items. Similarly, it is considered suitable for use in electrolyte restricted diets and does not contain sugar, fats, carbohydrates, lactose, gluten, yeast, corn, wheat starch, eggs, fish or dairy.

Although the concentrate has been shown and described in connection with a particular carrier for treatment, i.e., in an aqueous-based mixture, it is understood that the composition may be in other forms, whether in a non-aqueous-based mixture, in tablet form, in gel capsule form, in a fluid, or other conventional and non-convention al method of administration, as is practicable, giving consideration to the purpose for which the present invention is intended.

In addition, while the concentrate is disclosed with reference to particular ranges of constituents, it will be appreciated that other suitable ranges of ingredients may be utilized, giving consideration to the purpose for which the present invention is intended. For example, although the invention is described as containing particular B vitamins, other B vitamins and/or vitamins and nutrients generally may be utilized, within the spirit and scope of this disclosure.

Overall, the composition and method disclosed herein advantageously provides concentrated nutritional supplementation in a unique formula including B vitamins and vitamin C. It is formulated so as to be easily digestible and, therefore, rapidly absorbed to enhance delivery of its nutritionally balanced contents. In this manner, nutraceuticals important for good nutritional health and well-being, are now available in a unique, concentrated dose that is economical, easy to administer, safe and non-toxic.

In addition, relatively high levels of therapeutic ingredients are provided in a synergistic formulation at concentrations which optimize the body's function and utilization of each of these ingredients. The composition provides numerous additional beneficial features including, but not limited to, a composition that is rapidly absorbed by the body in solution, easily digestible such that the nutrients are readily available for absorption, and is well-tolerated by the body with no known side effects. Moreover, the composition according to the disclosure is formulated such that it is ready to use with no premixing required by the user.

Medical conditions and user groups believed to derive particular benefit from use of the above-described compositions, in accordance with the disclosure, include, but are not limited to: muscle atrophy, weakness, general fatigue and poor endurance; diabetes mellitus; nutritional deficiencies resulting from dieting; lipid abnormalities such as elevated cholesterol and/or triglyceride levels; and atherosclerosis/heart disease. The composition may also be used for preventing and/or countering the effects of Alzheimer's Disease, Chronic Fatigue Syndrome (CFS), Chronic Muscle Myopathy, Diabetes, Dieting, Epilepsy, Heart Disease, Immune Deficiency, Muscle Atrophy, Old Age, and Stroke.

Various modification s and alterations may be appreciated based on a review of this disclosure. These changes and additions are intended to be within the scope and spirit of the disclosure as defined by the following claims.

What is claimed is:

1. A nano concentrate, comprising composite nano particles, wherein molecules of $H_2O$ are encapsulated within a composite nano particle including selected nutrients, and the concentrate is a colorless, odorless, tasteless concentrate and is prepared by a method comprising the steps of:

collating and combining selected chemical constituents in powder form in a first container, wherein the selected chemical constituents comprise the selected nutrients:

mixing the selected chemical constituents in the first container for approximately 1 minute at an ambient pressure and a temperature generally within a range of 70 degrees F. and 75 degrees F. so as to produce a first premix comprising constituent particles in powder form:

transferring the first premix from the first container to a chamber of a size reduction apparatus for mechanically reducing a size of the constituent particles to nano scale:

operating the size reduction apparatus so as to produce a second premix comprising a nano emulsion of constituent particles between about 6 nanometers and about 20 nanometers in size:

transferring the second premix to a nano cooling apparatus: cooling the second premix in the nano cooling apparatus for about 10 minutes to about 30 minutes at the ambient pressure and a temperature generally within a range of 7 degrees C. and 12 degrees C.;

transferring the second premix to a second container; collating and combining a plurality of sealing ingredients including a selected anti solvent, sodium oleate and tetra methlvammonium-dodecvlamine each in liquid form and in an amount of between about 500 ml and about 700 ml in a third container;

mixing the sealing ingredients for approximately 1 minute to form mixed sealing ingredients;

allowing the mixed sealing ingredients to remain stationary for about 10 minutes to about 15 minutes at an ambient temperature and the ambient pressure;

transferring the mixed sealing ingredients to a fourth container;

collating and combining in the fourth container the second premix from the second container with the mixed sealing ingredients from the third container to form a first combination;

allowing the first combination in the fourth container to remain stationary and without influence from electrical shock for about 20 minutes to about 40 minutes at the ambient pressure and a temperature within a range of 60 degrees F. and 80 degrees F. so as to effect liquid sealing and a first bonding of constituents in the first combination and form a first sealed and bonded combination;

collating and combining about 1 liter of $H_2O$ purified by reverse osmosis with the first sealed and bonded combination in the fourth container;

mixing the $H_2O$ purified by reverse osmosis with the first sealed and bonded combination for approximately 1 minute to form a second combination;

allowing the second combination to remain stationary for about 30 minutes to about 60 minutes at the ambient temperature and pressure so as to enable a physical state transformation of the first sealed and bonded combination, wherein the first sealed and bonded mixture is transformed from a relatively solid nano powder form to a relatively thick clear nano liquid form of a first bonding protective sealed mixture, whereupon completion of the physical state transformation, a first bonding protective seal of the constituents is finalized, and the first bonding protective sealed mixture comprises particles each having a size of about 18 nanometers;

transferring the first bonding protective sealed mixture to a sterilization homogenization apparatus;

sterilizing the first bonding protective sealed mixture to form a sterilized first bonding protective sea led mixture;

allowing the sterilized-first bonding protective sealed mixture to remain stationary for about 20 minutes to about 40 minutes at the ambient temperature and pressure;

transferring the sterilized first bonding protective sealed mixture to a fifth container;

collating and combining about 1785 liters of $H_2O$ between about 7.5 PH and 9.5 pH, about 250 ml of 3-aminopropyltrimethoxvsilane (saline Aptms), and about 250 ml of oleic acid with the sterilized first bonding protective sealed mixture to form a fourth combination in the fifth container;

mixing the fourth combination for about 15 minutes to about 30 minutes to form a mixed fourth combination;

freezing the mixed fourth combination in the fifth container at the ambient pressure and a temperature generally within a range of 25 degrees 1 and 32 degrees F. for about 3 hours to about 4 hours so as to effect a relatively permanent second bonding of constituents of the first bonding protective sealed mixture to the molecules of $H_2O$, thawing the fourth combination frozen in the fifth container for about 4 hours to about 5 hours at the ambient temperature and pressure, so as to form a liquid concentrate, collating and combining the liquid concentrate with about 500 aril of mesoporous silica and about 500 ml of oleic acid to form a fifth combination; and mixing the fifth combination at the ambient pressure and temperature for up to about 2 minutes, so as to further stabilize and provide a second sealing protection to the relatively permanent second bonding of the constituents of the first bonding protective sealed mixture to the molecules of $H_2O$, and form the nano liquid concentrate, such that the composite nano particles in the nano liquid concentrate each has a size generally within a range of 12 and 16 nanometers, and the second sealing protection allows the composite nano particles in the nano liquid concentrate to have a stability of approximately 100%, wherein the selected nutrients are cannabidiol.

* * * * *